United States Patent [19]

Deskins et al.

[11] 4,388,594
[45] Jun. 14, 1983

[54] SEMI-PERMEABLE ELECTROLYTIC CELL AND METHOD FOR SURVEYING BURIED STRUCTURES

[75] Inventors: Robert L. Deskins, Huntington Beach; Gary L. Matlack, Ontario; Robert D. Ashbaugh, Mission Viejo, all of Calif.

[73] Assignee: Harco Corporation, Medina, Ohio

[21] Appl. No.: 157,678

[22] Filed: Jun. 9, 1980

[51] Int. Cl.³ .................. G01V 3/15; G01R 31/02; G01N 27/00
[52] U.S. Cl. ............................ 324/348; 36/1; 324/71.1; 324/72; 324/425
[58] Field of Search .......... 324/62, 65 P, 72, 347–349, 324/354, 357, 425, 450; 36/1

[56] References Cited

U.S. PATENT DOCUMENTS

| | | | |
|---|---|---|---|
| 1,163,469 | 12/1915 | Schlumberger | 324/348 |
| 2,256,742 | 9/1941 | Jakosky | 324/347 |
| 2,400,678 | 5/1946 | Archie | 324/347 X |
| 2,974,276 | 3/1961 | Davis | 324/348 X |
| 3,735,249 | 5/1973 | Stoll | 324/348 |
| 4,151,458 | 4/1979 | Seager | 324/72 X |

Primary Examiner—Gerard R. Strecker
Attorney, Agent, or Firm—Maky, Renner, Otto & Boisselle

[57] ABSTRACT

An apparatus and method of conducting continuous or closely spaced buried structure-to-soil electrical surveys uses a soil contact cell adapted to be worn on the bottom of the walking field boots of a surveyor walking over the right-of-way of the buried structure such as an underground pipeline. The cell is in the form of a sandal which may readily be secured to and removed from the bottom of the boot. The cell includes an impervious upper plate and a pervious lower ground contacting flexible sole plate forming with the upper plate a flat chamber which may be filled with a loose silica sand fill or sponge material. A copper rod or strap is imbedded in the material and electrically connected through a meter carried by the surveyor to the structure through a length of economically disposable wire. The surveyor carries a supply of conductive liquid such as a copper sulfate solution which is fed into the chamber and through the porous sole plate to the ground to ensure good electrical contact as the surveyor walks the right-of-way.

36 Claims, 10 Drawing Figures

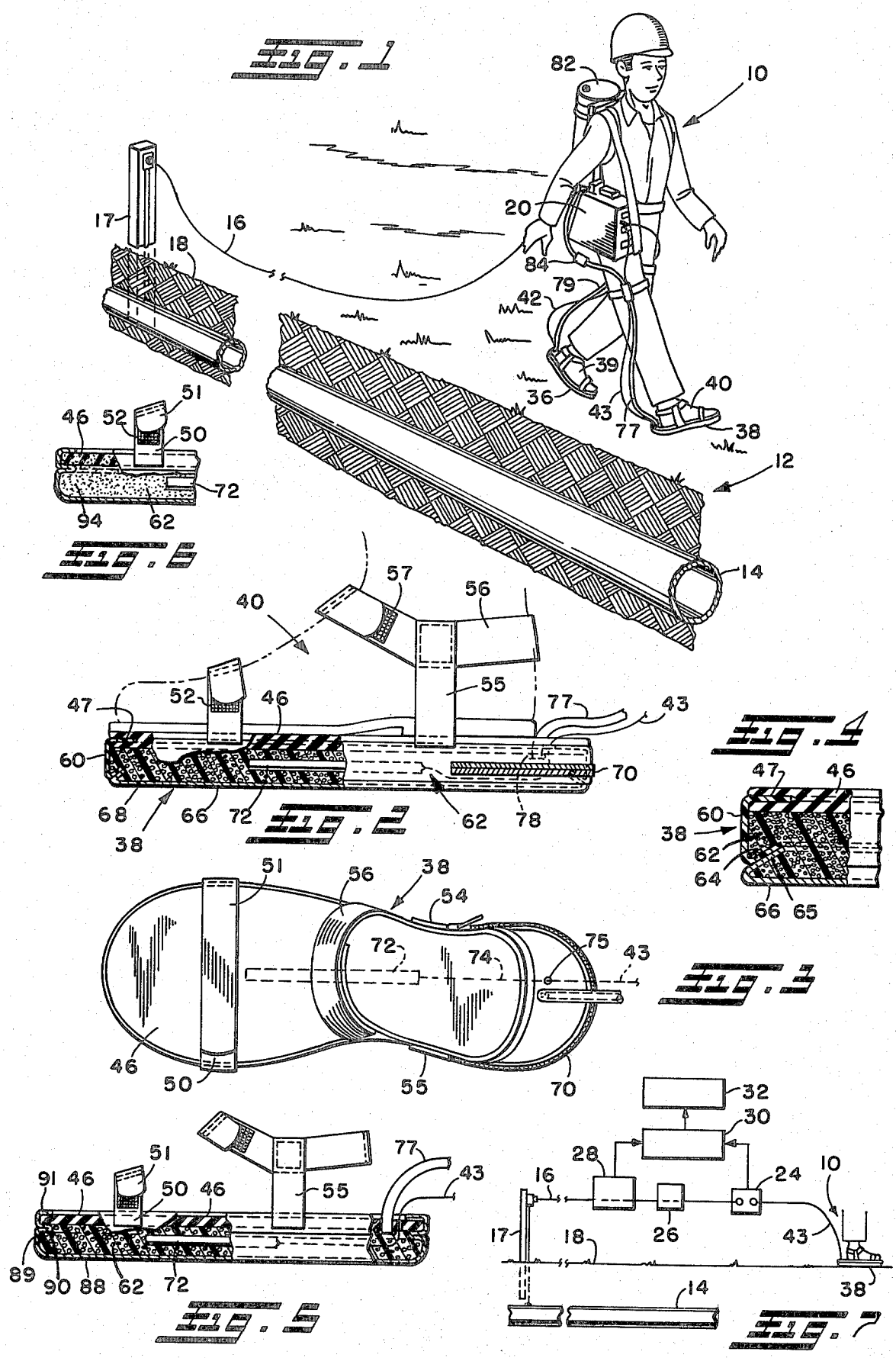

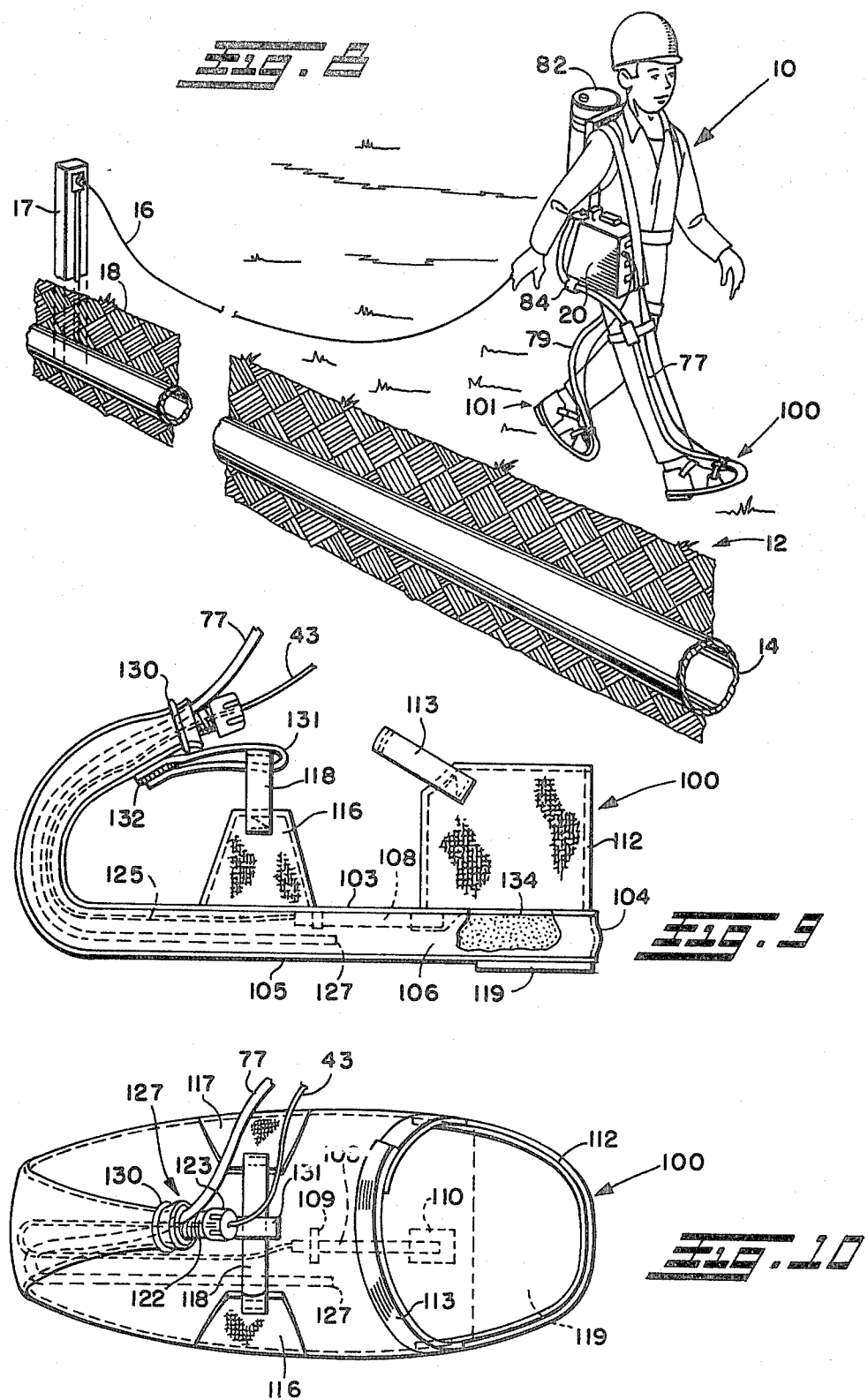

SEMI-PERMEABLE ELECTROLYTIC CELL AND METHOD FOR SURVEYING BURIED STRUCTURES

BACKGROUND OF THE INVENTION

The present invention relates generally as indicated to structure-to-soil potential difference surveys such as disclosed in prior U.S. Pat. No. 4,151,458 to William H. Seager.

Closely spaced pipe-to-soil potential surveys are conducted periodically of buried structures such as pipeline to monitor cathodic protection and to locate areas of potential problems.

Such electrical surveys require a contact to the pipe, a suitable voltmeter or potentiometer, and a means of contacting the ground. A copper-copper sulfate (Cu-CuSO$_4$) cell is an industry standard for providing the necessary contact with the ground. Such cells or electrodes are illustrated in the above-noted Seager U.S. patent. Reference may also be had to the early Schlumberger U.S. Pat. No. 1,163,469 for a further illustration of such type of electrode. Such electrodes are usually mounted on the lower end of a pole or cane which is hand held by the surveyor.

Such electrodes have a relatively small area of contact resulting in rather high contact resistance between the electrode or reference cell and the earth. If the resistance between the reference electrode and the earth is relatively high and, therefore, represents a significant portion of the total circuit resistance, then the voltmeter in the circuit will read a significantly lower voltage value than actually exists between the reference cell and the structure which is being monitored. Generally the resistance of the metal paths including the lead wire and the metal structure are relatively small and the only two significant resistances exist at the voltmeter and at the contact between the cell or electrode and the earth. As an example, if the measuring voltmeter has an effective resistance of one million ohms and the reference cell resistance is 500,000 ohms, the voltmeter then only registers two-thirds of the actual voltage difference that exists between the reference cell and the structure in the earth. This is a particular problem in dry soils, sandy soils or rock laden areas. Readings become a small fraction of what they should be.

Moreover, when the reference cell is hand held as indicated in the noted prior art, the surveyor generally tries to force the electrode against the earth to obtain good contact. After a few kilometers of surveying in dry, sandy or rocky areas, the surveyor's arms begin to feel like a boxer's in the fifteenth round.

The problems encountered when surveying under dry conditions have long been recognized as seen, for example, in Jakosky U.S. Pat. No. 2,105,247 wherein a spray is employed to dampen the surface of the earth next to the contacts. The same inventor in U.S. Pat. No. 2,256,742 has also suggested that, in short surveys where the soil affords good surface contact, a man may be provided with contact plates attached to his feet. While the particular construction of the plates is not described, it is apparent that the contacts are not intended for areas where the soil affords poor surface contact nor can such plates provide the reduced reference electrode contact resistance which is afforded by the industry standard copper-copper sulfate (Cu-CuSO$_4$) cell.

SUMMARY OF THE INVENTION

With the present invention electrical surveys of buried structures may readily be accomplished by utilizing copper-copper sulfate cells readily attached to field boots of the surveyor. Rather than being rigid plates the cells are highly flexible and conform to any irregularities in the surface of the earth beneath the boot of the surveyor. They also provide a substantially larger reference electrode contact surface area than achieved with conventional pole or cane mounted reference electrodes, thus reducing contact resistance between the reference cell and earth.

Being readily affixed to the underside of the field boot, the cell permits the surveyor complete freedom of action and results in not only greater down pressure but also a larger contact area.

The cell or electrode is in the form of a sandal readily worn by the surveyor and includes an impervious upper plate on which the sole of the boot is secured. The plate may be of a material similar to a shoe sole and is somewhat flexible although fairly thick and impervious. The material is preferably non-conductive. Secured to the upper plate is a pervious lower ground contacting flexible sole plate forming with the upper plate a flat shallow chamber which may be filled with a loose silica sand fill, sponge or foam material. A copper rod or strap is imbedded in the material and electrically connected through a meter carried by the surveyor to the structure through a length of economically disposable wire. A small plastic tube extends into the chamber from a supply of conductive solution or electrolyte carried by the surveyor.

The electrolyte such as copper sulfate inside the fill material can readily be replenished from the reservoir through the small tube either by control of a manual valve or by the use of a small pump and check valve.

The bottom sole plate of the sandal may be of a porous material such as firehose canvas without the rubber liner. Such a material is not only wear resistant but has a low fluid transmission rate thus reducing the possibility of contamination by outside environment of the electrolyte in the chamber which might tend to distort the cell readings. The low transmission rate also keeps the necessary electrolyte inside the chamber from leaking out at too high a rate which would cause undue consumption of the make-up supply carried by the surveyor.

The sides of the chamber from the top plate to the bottom plate may be formed of canvas or an impervious material such as vinyl sheet. In a preferred form, the chamber may be formed with an openable and closable extended flexible toe for recharging and entrance of wiring and tubing into the chamber. The extended toe is equipped with a loop so that it may be folded back over the toe of the boot of the surveyor and secured in place when closed. In another form the sidewall of the chamber formed between the two plates may be provided with a zippered opening so that the contents of the chamber may be removed and replaced.

Straps may be provided extending from cloth extensions on the top of the upper plate so that the sandal-like electrode may readily be secured to the underside of a field boot. A VELCRO fastening system is preferred which readily adapts the straps so that the sandal-cell may quickly and readily be firmly secured to substantially any size field boot. VELCRO is a trademark of Velcro U.S.A. Inc., New York, N.Y. used for its hook and loop fastening systems which are widely used and well know as adjustable fasteners. These fastening systems are capable of repeated separation and rejoining.

In summary, the foot worn cell or electrode is comfortable, easily put on and removed, significantly reduces contact resistance problems, and is adjustable to most size feet or boots. Moreover, the fluid within the cell is designed continuously to pass through the flexible porous bottom and such fluid is continually replenished as required on a manually or automatically controlled basis.

It is accordingly a principal object of the present invention to provide a cell for closely spaced or continuous structure-to-soil surveys which substantially reduces electrical contact resistance.

It is another principal object to provide such cell which is particularly useful in dry, sandy or rocky soils.

Another object is the provision of a foot worn cell which has the advantages of the industry standard copper-copper sulfate cell but which nonetheless still avoids contact resistance problems.

Another important object is the provision of such foot worn cell which is comfortable, easily put on and taken off, and adjustable to many size field boots.

Yet another object is the provision of an electrolytic cell for conducting field surveys of buried structures which leaves both of the hands of the surveyor free.

Another object is the provision of such cell and survey technique wherein the electrolyte in the cell may continually be replenished as required.

A still further object is the provision of a survey when the electrolyte may be replenished on an automatic or manual basis.

Other objects and advantages of the present invention will become apparent as the following description proceeds.

To the accomplishment of the foregoing and related ends the invention, then, comprises the features hereinafter fully described and particularly pointed out in the claims, the following description and the annexed drawing setting forth in detail certain illustrative embodiments of the invention, these being indicative, however, of but a few of the various ways in which the principles of the invention may be employed.

BRIEF DESCRIPTION OF THE DRAWING

In said annexed drawing:

FIG. 1 is broken perspective view illustrative of one form of the cells of the present invention in use during a survey being conducted;

FIG. 2 is a side elevation partially broken away and in section of a cell in accordance with the present invention;

FIG. 3 is a top plan view of the cell;

FIG. 4 is a fragmentary transverse section of the edge of the cell;

FIG. 5 is a view similar to FIG. 2 of a slightly modified form of the cell;

FIG. 6 is a further fragmentary broken illustration of another form of the cell in accordance with the present invention;

FIG. 7 is a schematic illustration of the cell in use and the electrical connections between the cell and the buried structure;

FIG. 8 is a view similar to FIG. 1 of a preferred form of cell of the present invention in use;

FIG. 9 is an enlarged side elevation of the cell of FIG. 8; and

FIG. 10 is a top plan view of the cell of FIG. 9.

DESCRIPTION OF THE PREFERRED EMBODIMENTS

Referring now in detail to the drawing and initially to FIG. 1, there is illustrated a surveyor shown generally at 10 conducting a survey in accordance with the present invention. The surveyor is alone and is walking over the right-of-way 12 of a buried structure 14 which as illustrated is a subsurface pipeline.

The surveyor is trailing behind him along the right-of-way a small gauge economically disposable wire 16 which is connected behind the surveyor to a test lead station 17 which projects above the surface of the earth 18 on the right-of-way 12. The test lead station 17 provides a convenient electrical connection to the pipeline at a known location. The test lead station 17 is usually one of many installed at known locations along the pipeline right-of-way at periodic intervals of from 2 to 3 kilometers, for example. The wire 16 is preferably enamelled copper magnet wire and is of light weight such as shown and described in the aforementioned Seager U.S. Pat. No. 4,151,458. The wire is sufficiently light weight that the surveyor 10 may carry with him several spools of the wire which may readily be spliced together.

The spools may be carried in the case 20 carried by the surveyor with the assistance of shoulder strap 21.

Referring momentarily to FIG. 7 it will be seen that the case 20 carried by the operator may include a meter 24, a wire supply 26, and a wire length transducer or location determining device 28. Both the transducer 28 and the meter 24 feed information to a microcomputer control device 30 which in turn feeds the information obtained to a data storage medium 32.

The meter may be a conventional digital difference meter capable of being automatically read by a computer, or it may be an analog to digital converter with appropriate input signal conditioning circuitry or the equivalent means to provide information understood by the computer to represent the potential difference information.

The wire length transducer 28 automatically feeds data to the computer representing the length of wire paid out, which is a representation of the distance of the surveyor from a known location or test station 17.

The data storage medium may be a solid state battery powered magnetic tape or disc information storage medium or the equivalent. After the data is obtained in the storage medium 32 it may subsequently be processed through a computer to obtain a graphic print-out of the information obtained by the survey. Reference may be had to the copending application of Joseph Rog et al., Ser. No. 017,180, filed Mar. 5, 1979, entitled "Electrical Survey Apparatus and Method," assigned to Harco Corporation of Medina, Ohio for a more detailed description of the components which may be carried by the surveyor and their utilization to obtain electrical surveys of the buried structure.

The meter 24 is also electrically connected to reference electrodes or cells 36 and 38 worn on the bottom of the field boots 39 and 40 of the surveyor 10. Electrical connection may be through small gauge insulated wires seen at 42 and 43.

The electrodes or cells 36 and 38 are in the form of sandals worn by the operator beneath the normal field boots or shoes and a preferred form is shown in FIGS. 2-4. With reference to such figures it will be seen that the electrode or cell 38 comprises a top plate 46 which is impervious and may be made of rubber or neoprene, for example. The top plate includes a peripheral center edge slot 47. In such slot are secured straps 50 and 51 designed to go over the front of the field boot 40 and which may be secured together by a suitable fastening system such as the VELCRO system illustrated at 52. Also secured in such slot are straps 54 and 55 which are connected at their free or distal ends to generally horizontally extending loop strap 56 which is designed to go around the upper portion of the field boot and which is secured upon itself at the top of the field boot again by the VELCRO fastening system seen at 57. The straps 50, 51, 54 and 56 may be secured in the edge slot of the top plate 46 by stitching or suitable adhesive fastening methods. In any event with the straps and fastening system illustrated, the sandal may readily be secured to substantially any size field boot.

Also secured in the edge slot by stitching or such suitable adhesive fastening methods is a vinyl or rubberized sheet 60 which extends outwardly and is folded down from the edge of the top plate to form a sidewall for a chamber shown generally at 62 beneath the top plate 46. The lower edge of the vinyl wall is folded inwardly as seen at 64 and is lap secured to a similar inwardly folded edge 65 of a bottom plate 66. The bottom plate 66 may be porous as opposed to the impervious nature of the top plate 46. As a preferred form of material for the bottom plate, firehose canvas is employed. The chamber 60 formed by the top plate 46, the sidewall 60 and the bottom plate 66 may be filled with an open pore sponge or foam material or silica sand seen at 68. The sponge material may, for example, be a relatively flexible and soft material such as natural sponge, polyvinyl sponge or a polyurethane sponge.

At the heel portion of the sandal or cell the peripheral wall 60 may be provided with a plastic zipper seen at 70 which permits the chamber 62 to be opened to provide access to the interior thereof. The plastic zipper when closed normally provides a substantially watertight continuation of the wall 60.

Situated within the medium of the sponge material 68 is a copper rod 72 which is spaced both from the top plate 46 and the bottom porous plate 66. The copper rod extends from a position substantially beneath the ball of the foot of the field boot wearer to a position just ahead of the heel of the wearer. The copper rod is connected by a suitable wire seen at 74 to the insulated wire 43 which exits through the top plate in sealed condition seen at 75. The exit for the wire is behind the heel of the field boot.

Also behind the heel of the field boot a flexible plastic tube seen at 77 extends through the top plate and is secured and sealed through the top plate as indicated at 78. The other cell or electrode worn by the surveyor is similarly provided with a plastic tube seen at 79 in FIG. 1. Both such plastic tubes are connected to a container 82 which the surveyor carries on his back. The container 82 may be plastic and contain several liters of highly conductive solution such as copper sulfate. The container 82 preferably supplies the chamber of each cell or electrode through a gravity feed which may be regulated through a suitable valve seen at 84. The valve 84 may be in the form of a wedge type pinch valve conventionally employed with intravenous drip solutions. If the surveyor feels he needs more solution in the cells he simply opens the valve a notch or two to permit more fluid to flow by gravity through the plastic tubes into the chambers of the cells. Alternatively, the plastic tubes may be provided with bulb type pumps and associated check valves by means of which the surveyor may pressure force fluid into the cells. A check valve may also be provided in association with the valve to prevent back flow when the surveyor places his full weight on the cell thus reducing the volume of the chamber. In any event the porosity of the bottom plate such as the firehose canvas is designed so that the exterior of the plate remains wet as the surveyor walks over the right-of-way 12. In particularly dry conditions, the bottom surface of the plate 66 may be required to maintain its wetness to a greater degree than if the surveyor is walking over moist or normal soil conditions.

It will be appreciated that as the surveyor places his weight on the cell or electrode, the volume of the chamber 62 is reduced or compressed and fluid within the chamber is forced outwardly. This maintains the exterior surface of the bottom plate wet. It will be appreciated also that other forms of porous bottom plates may be provided but preferably plates which will not contaminate the fluid within the chamber when such pressure is relieved.

Referring now to FIG. 5 it will be seen that the sandal-cell may be constructed such that the porous bottom wall 88 formed of firehose canvas or the like also forms the peripheral wall seen at 89, such wall being folded both beneath and above the top plate 46 as seen at 90 and 91, respectively, and is stitched thereto. In this manner the separate vinyl or impervious sidewall for the chamber 62 is not provided. The sandal electrode or cell otherwise remains the same. With the embodiment of FIG. 5 a peripheral or edge groove in the top plate 46 is not required. The straps 52, 51, 55 and 54 may be simply secured to and stiched beneath the top plate 46.

With reference to FIG. 6, a similar construction is employed. However, in lieu of the sponge or open cell porous foam material employed as the medium within the chamber, a loose fill material seen at 94 is employed to fill the chamber 62. Such fill material may be in the form of sand, vermiculite, or other loose fill material which will nonetheless maintain the fluid consistency of the copper sulfate or other solution in the chamber. With such loose fill material, the surveyor is essentially walking on something similar to sand bags saturated with the solution from the container 82. It is however desirable that the weight or density of the fill material not excessively contribute to the weight of the cell.

The copper rod 72 may also be in the form of a copper strap to provide a certain degree of flexibility to conform to the pressure applied by the ball and heel of the foot of the surveyor. The copper rod or electrical connection may also be in the container 82 with the current passing through the solution in the chamber and in the tube to form what is known as a "salt bridge".

Referring now to the embodiment of FIGS. 8, 9 and 10 it will be seen that the cells worn by the surveyor 10 and shown generally at 100 and 101 each comprise a somewhat more flexible and thinner top plate 103. Secured to the top plate are canvas sides 104 and a canvas bottom 105 forming chamber 106. A copper rod or strap 108 is secured to the underside of the top plate 103 by hold-down straps 109 and 110. The rod or strap 108 extends from the ball of the foot of the wearer to just ahead of the heel.

Secured to the top of the plate 103 at the heel is a heel cup heavy cloth extension seen at 112 and a strap connects the projecting corners as seen at 113. The strap may be provided with a VELCRO fastening system. Also extending upwardly from the top plate 103 are two truncated triangular heavy cloth cloth extensions 116 and 117 and again such extensions are interconnected over the top of the forepart of the boot of the wearer by the straps seen at 118 again provided with a VELCRO fastening system. The extensions 112, 116 and 117 may be reinforced. For wear resistance, the bottom plate 105 may be provided with a leather heel cap seen at 119.

Both the top and bottom plates 103 and 105 are somewhat pointed as they extend beyond the toe and form an openable and closable opening indicated generally at 121. A plastic fitting seen at 122 extends through the opening in the closed condition and may be provided with a removable cap 123. Extending through the fitting is lead wire 125 which may be connected to or form an extension of the wire 43 connecting the cell to the meter. Also extending through the closable opening is flexible tubing 77 which extends to approximately the center of the chamber as seen at 127. The toe opening of the chamber may be closed and secured by a copper wire strap or cinch 130. When the chamber is closed by such strap the flexible nature of the top and bottom walls permits the toe of the chamber to be folded back over the toe of the boot of the surveyor. The flexible closed toe may then be secured in place to the strapping 118 by the loop strap 131 again provided with a VELCRO fastening system seen at 132. The interior of the chamber even through the flexible folded back toe may be provided with a matrix of silica sand as seen at 134. When in use the appearance is somewhat like a rather heavy slipper from the Arabian Nights.

With the preferred embodiments of FIGS. 8, 9 and 10 the extended open toe can readily be used for recharging the fill material into the chamber and also for the entrance of wiring and tubing. The pointed toe is equipped with a loop so that when it is folded back over the toe of the boot, it can be strapped in place with the VELCRO fastening system to secure the closed opening in place. In this manner the folded back open toe arrangement permits the avoidance of openings, holes, or zippers in the sole plate or in the chamber walls.

It is noted that the cells of FIGS. 8-10 are not right or left footed and that the VELCRO fastening system 132 permits the flexible open toe 121 to be folded back over the top of substantially any size boot.

In any event it can now be seen that the surveyor utilizes a cell providing a considerably larger reference electrode contact surface area than achieved with conventional reference electrodes thus reducing the contact resistance between the reference cell and the earth. Moreover, the cell permits the wearer or surveyor complete freedom of action and results in a much more forcible down pressure being applied to the reference electrode contact surface than can be achieved by the more conventional hand-held reference electrode technique.

The cell or electrode is designed to be flexible and to be readily worn beneath a pair of standard field boots. The flexibility provides for easy walking comfort. It also conforms to variations in the earth surface of the survey.

The invention also results in an extremely high pressure being exerted by the surveyor especially beneath the heel and ball of the surveyor's foot. With the porous canvas assembly, the cooper reference element is contained within a soft, flexible electrolyte filler such as sponge, sand or other suitable media.

The cells or electrodes are readily put on various size boots through the use of the strapping system. The firehose canvas or other porous bottom wall serves several purposes. These include a low fluid transmission rate thus reducing the possibility of contamination by the outside environment of the electrolyte inside the cell or electrode which would distort the readings obtained. This same low transmission rate also keeps the necessary copper-copper sulfate solution or other suitable electrolyte inside the cell chamber from leaking out at too high a rate which would cause high consumption of the back-pack carried electrolyte supply.

Moreover, the sandal-cells are adjustable to many size feet and assure that at least one cell is always in contact with the ground since in a normal walking mode one or both feet are always in contact with the earth. The reservoir 82 provides a continuously replenished electrolyte. It will however be appreciated that for shorter surveys the reservoir may not be necessary. The surveyor may simply periodically replenish the electrolyte from a container such as a canteen.

Although the invention has been shown and described with respect to a preferred embodiment, it is obvious that equivalent alterations and modifications will occur to others skilled in the art upon the reading and understanding of this specification. The present invention includes all such equivalent alterations and modifications, and is limited only by the scope of the claims.

The embodiments of the invention in which an exclusive property or privilege is claimed are defined as follows:

1. A process of performing electrical surveys of buried structures comprising the steps of connecting a wire with respect to the buried structure, and then walking on the surface over the structure on an electrically conductive liquid cell while the wire is paid out along the structure, said cell being in the form of footwear for at least one foot of the surveyor and connected to such wire through a meter for measuring pipe to soil type potential difference to obtain such survey.

2. A process as set forth in claim 1 including a cell for each foot, each cell being connected to the wire through such meter.

3. A process as set forth in claim 1 wherein such cell is a copper-copper sulfate cell.

4. A process as set forth in claim 3 including the step of causing the salt solution to percolate through the bottom of the cell to maintain the bottom of the cell moist during the survey.

5. A process as set forth in claim 4 including the step of replenishing the salt solution in the cell as the survey progresses.

6. A process as set forth in claim 5 including the step of replenishing the salt solution in the cell at a controlled rate from a supply of such solution carried by the surveyor.

7. A process as set forth in claim 6 including the step of incorporating a fill medium in the cell surrounding the metal, such fill medium being flexible to conform to the surface.

8. A process as set forth in claim 1 wherein such cell is in the form of a pair of sandals which may readily be attached to and removed from the footwear of the surveyor.

9. A process as set forth in claim 8 wherein the surveyor walks in a normal walking mode to insure that one or both cells are always in contact with the surface.

10. A liquid cell for conducting surveys of buried structures comprising a chamber, means coupled to the chamber for introducing an electrolyte, said chamber including a substantially impervious upper plate and a semi-permeable lower plate thereby forming said chamber; a metallic conductor positioned within said chamber and having a conductor lead which extends to an outer surface of said chamber; and securing means coupled to said cell for removably attaching said cell to at least one foot of a surveyor.

11. A cell as set forth in claim 10 in the form of a sandal where said securing means are straps attached to said chamber and adapted to be secured about the footwear of a surveyor.

12. A cell as set forth in claim 11 wherein said chamber is a flat shallow chamber.

13. A cell as set forth in claim 12 wherein such chamber is filled with a flexible filler material.

14. A cell as set forth in claim 13 wherein such filler material is loose.

15. A cell as set forth in claim 13 wherein such filler material is an open cell sponge.

16. A cell as set forth in claim 13 wherein said metallic conductor is a copper rod or strap embedded in such filler material parallel to the top plate.

17. A cell as set forth in claim 16 wherein said copper rod or strap extends from the ball of the foot of the wearer to the heel.

18. A cell as set forth in claim 16 wherein said conductor lead extends from the rod or strap through the top plate behind the heel of the wearer.

19. A cell as set forth in claim 16 wherein said cell includes an open toe adapted to be closed and folded back.

20. A cell as set forth in claim 12 said means for introducing comprising a flexible tube extending into such chamber, and means to feed liquid to such chamber through said tube.

21. A cell as set forth in claim 20 including a supply of liquid carried by the surveyor, to which said tube is connected.

22. A cell as set forth in claim 21 including a valve operative to control the rate of flow through said tube to such chamber.

23. A cell as set forth in claim 21 wherein said supply of liquid is copper sulfate.

24. A cell as set forth in claim 12 wherein said chamber includes an impervious sidewall secured to said top and bottom plates.

25. A cell as set forth in claim 24 including a zipper opening in said sidewall permitting access to the interior of such chamber.

26. A cell as set forth in claim 25 wherein said zipper is plastic and at the back of the heel.

27. A cell as set forth in claim 12 wherein the impervious upper plate is rubber.

28. A cell as set forth in claim 12 wherein the semi-permeable lower plate is canvas.

29. A cell as set forth in claim 28 wherein said conductor lead extends from the rod or strap through the open toe.

30. A cell as set forth in claim 12 said securing means including straps secured to the upper plate to secure the plate beneath the footwear of the surveyor.

31. A cell as set forth in claim 30 including a VELCRO fastening system for said straps.

32. A cell as set forth in claim 12 wherein the lower plate extends upwardly at its sides and is secured to the edge of the top plate by fastener means which comprise stitching or an adhesive, or a combination thereof.

33. A cell as set forth in claim 12 wherein said cell includes an open toe adapted to be closed and folded back over the top of the footwear of the surveyor.

34. A cell as set forth in claim 33 including means to secure the folded back toe in such folded back condition.

35. A cell as set forth in claim 33 wherein said metallic conductor includes a copper rod or strap in such chamber, and a lead wire extending to such rod or strap through the open toe.

36. A cell as set forth in claim 33 said means for introducing including a flexible electrolyte supply tube extending into such chamber through the open toe.

* * * * *